(12) United States Patent
Winter

(10) Patent No.: US 11,633,617 B2
(45) Date of Patent: Apr. 25, 2023

(54) DEVICE AND METHOD FOR GENERATING A PLASMA JET

(71) Applicant: LEIBNIZ-INSTITUT FÜR PLASMAFORSCHUNG UND TECHNOLOGIE E.V., Greifswald (DE)

(72) Inventor: Jörn Winter, Greifswald (DE)

(73) Assignee: LEIBNIZ-INSTITUT FÜR PLASMAFORSCHUNG UND TECHNOLOGIE E.V., Greifswald (DE)

( * ) Notice: Subject to any disclaimer, the term of this patent is extended or adjusted under 35 U.S.C. 154(b) by 1088 days.

(21) Appl. No.: 16/330,090

(22) PCT Filed: Jul. 26, 2017

(86) PCT No.: PCT/EP2017/068913
§ 371 (c)(1),
(2) Date: Mar. 3, 2019

(87) PCT Pub. No.: WO2018/041483
PCT Pub. Date: Mar. 8, 2018

(65) Prior Publication Data
US 2019/0232073 A1    Aug. 1, 2019

(30) Foreign Application Priority Data

Sep. 2, 2016 (EP) .................... 16187095

(51) Int. Cl.
*A61N 1/44* (2006.01)
*A61L 2/14* (2006.01)
(Continued)

(52) U.S. Cl.
CPC ............... *A61N 1/44* (2013.01); *A61B 1/015* (2013.01); *A61B 18/042* (2013.01);
(Continued)

(58) Field of Classification Search
None
See application file for complete search history.

(56) References Cited

U.S. PATENT DOCUMENTS 5,403,453 A * 4/1995 Roth ................. H01J 37/32174
204/164
5,444,331 A * 8/1995 Matsuno ................. H01J 61/26
313/634
(Continued)

FOREIGN PATENT DOCUMENTS

DE    10 2009 028462    3/2011
DE    102010061059 A1   4/2012
(Continued)

OTHER PUBLICATIONS

Stephan Reuter et al: 11 Controlling the Ambient Air Affected Reactive Species Composition in the Effluent of an Argon Plasma Jet 11, IEEE Transactions On Plasma Science, IEEE Service Center, Piscataway, NJ, US, vol. 40, No. 11, Nov. 1, 2012 (Nov. 1, 2012), pp. 2788-2794, XP011471648, ISSN: 0093-3813, DOI:10.1109/TPS.2012.2204280 p. 2789, left-hand column, line 30—p. 2793, left-hand column, line 2, figures 2,8,10.

(Continued)

*Primary Examiner* — Srinivas Sathiraju
(74) *Attorney, Agent, or Firm* — Soroker Agmon Nordman

(57) ABSTRACT

The invention relates to a device (10) for generating a plasma jet (P) comprising a first conduit (11) inside a second conduit (12), a first electrode (17) and a second electrode (18) for generating an electric field in a feed gas flow (F) provided in a first flow channel (15) to generate a plasma jet (P), and adapted to provide a curtain gas flow (C) in the space between the first and second conduit (11,12), wherein the first electrode (17) is positioned radially outside of the first flow channel (15), and wherein the radial distance of the (Continued)

Figure 1:
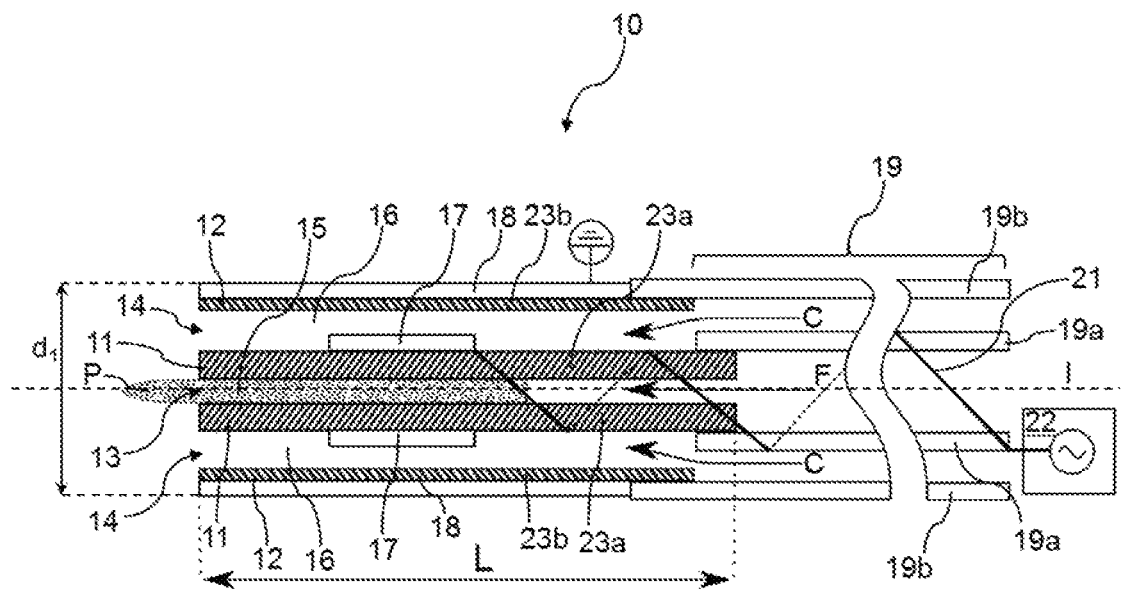

second electrode (18) from a longitudinal axis (I) is larger than the radial distance of the first electrode (17) from said longitudinal axis (1).

The invention further relates to an endoscope comprising a device (10), a method for generating a plasma jet (P), a method and a use of the device (10) for manipulating a cavity.

14 Claims, 2 Drawing Sheets

(51) Int. Cl.
    *H05H 1/24*     (2006.01)
    *A61L 2/00*     (2006.01)
    *A61B 18/04*     (2006.01)
    *A61B 1/015*     (2006.01)

(52) U.S. Cl.
    CPC .............. *A61L 2/0011* (2013.01); *A61L 2/14* (2013.01); *H05H 1/2406* (2013.01); *A61L 2202/11* (2013.01); *H05H 1/2431* (2021.05); *H05H 1/2443* (2021.05); *H05H 2245/32* (2021.05)

(56) References Cited

U.S. PATENT DOCUMENTS

| | | | | |
|---|---|---|---|---|
| 6,406,759 | B1* | 6/2002 | Roth | H05H 1/466 134/1.1 |
| 7,432,470 | B2* | 10/2008 | Kumar | H05H 1/46 219/121.48 |
| 8,475,451 | B2 | 7/2013 | Cho | |
| 8,668,687 | B2* | 3/2014 | Johnson | A61B 18/042 606/41 |
| 9,192,040 | B2* | 11/2015 | Ehlbeck | H05H 1/24 |
| 9,498,637 | B2* | 11/2016 | Sanders | A61L 2/14 |
| 9,511,240 | B2* | 12/2016 | Dobrynin | A61N 1/44 |
| 9,532,826 | B2* | 1/2017 | Sartor | A61B 17/00234 |
| 9,558,918 | B2* | 1/2017 | Watson | A61L 2/14 |
| 9,627,167 | B2* | 4/2017 | Yu | H05H 1/48 |
| 10,237,962 | B2* | 3/2019 | Thompson | H05H 1/46 |
| 10,446,373 | B2* | 10/2019 | Zimmerman | H05H 1/50 |
| 11,006,994 | B2* | 5/2021 | Krasik | A61B 1/018 |
| 2002/0100751 | A1* | 8/2002 | Carr | H05H 1/30 219/121.36 |
| 2003/0031610 | A1* | 2/2003 | Ricatto | C10G 35/16 422/186.04 |
| 2004/0012319 | A1* | 1/2004 | Shun'ko | H01J 37/32091 313/361.1 |
| 2004/0044342 | A1* | 3/2004 | Mackay | A61B 18/042 606/49 |
| 2005/0001527 | A1* | 1/2005 | Sugiyama | H01J 37/32082 315/111.21 |
| 2006/0189976 | A1* | 8/2006 | Kami | H05H 1/2406 606/41 |
| 2011/0018444 | A1* | 1/2011 | Pouvesle | H05H 1/2406 315/111.21 |
| 2011/0301412 | A1* | 12/2011 | Cho | A61N 1/44 606/41 |
| 2013/0053760 | A1* | 2/2013 | Ehlbeck | H05H 1/24 422/186.04 |
| 2013/0053762 | A1* | 2/2013 | Rontal | A61B 1/015 604/24 |
| 2013/0068226 | A1* | 3/2013 | Watson | A61L 2/0011 128/203.29 |
| 2013/0071286 | A1* | 3/2013 | Watson | A61L 2/0094 315/111.21 |
| 2013/0072858 | A1* | 3/2013 | Watson | H01J 37/32348 604/23 |
| 2013/0072859 | A1* | 3/2013 | Watson | A61M 16/06 604/23 |
| 2013/0072860 | A1* | 3/2013 | Watson | A61L 2/00 604/23 |
| 2013/0072861 | A1* | 3/2013 | Watson | A61L 2/00 604/23 |
| 2013/0204244 | A1* | 8/2013 | Sakakita | H05H 1/24 315/111.21 |
| 2014/0005481 | A1* | 1/2014 | Rontal | A61B 18/042 604/20 |
| 2015/0038790 | A1* | 2/2015 | Rontal | A61B 1/0051 604/20 |
| 2015/0366042 | A1* | 12/2015 | Zaidi | H05H 1/2406 315/111.21 |
| 2015/0373824 | A1* | 12/2015 | Nettesheim | H01L 41/107 315/111.21 |
| 2016/0121134 | A1* | 5/2016 | Kalghatgi | H05H 1/2406 604/23 |
| 2016/0137529 | A1* | 5/2016 | Cho | H05H 1/52 315/111.21 |
| 2019/0232073 | A1* | 8/2019 | Winter | A61L 2/0011 |
| 2021/0299461 | A1* | 9/2021 | Guy | A61B 1/00089 |
| 2021/0316106 | A1* | 10/2021 | Canady | A61M 16/024 |
| 2021/0316153 | A1* | 10/2021 | Canady | A61M 16/0833 |
| 2021/0338304 | A1* | 11/2021 | Krasik | A61B 18/042 |

FOREIGN PATENT DOCUMENTS

| | | | |
|---|---|---|---|
| EP | 1293169 | B1 | 7/2006 |
| JP | 2002112948 | A | 4/2002 |
| WO | 2005125286 | A2 | 12/2005 |
| WO | WO-2005125286 | A2 * | 12/2005 .......... H05H 1/2406 |
| WO | 2006/119892 | A1 | 11/2006 |
| WO | 2007/105428 | A1 | 9/2007 |
| WO | 2011/015538 | A1 | 2/2011 |
| WO | 2011/092186 | A1 | 8/2011 |
| WO | 2016071680 | A1 | 5/2016 |

OTHER PUBLICATIONS

Bekeschus Sander et al: 11 Ni trogen Shielding of an Argon Plasma Jet and Its Effects on Human Immune Cells 11, IEEE Transactions On Plasma Science, IEEE Service Center, Piscataway, NJ, US, vol. 43, No. 3, Mar. 1, 2015 (Mar. 1, 2015), pp. 776-781. XP011574493, ISSN: 0093-3813, DOI: 10.1109/TPS.2015.2393379 [retrieved on Mar. 6, 2015] p. 776, right-hand column, line 40—p. 777, left-hand column, line 21.

Anonymous: 11 Search Results 11 ,A—Feb. 14, 2017 (Feb. 14, 2017),XP055345847,Retrieved from the Internet: URL:http://webbook.nist.gov/cgi/cbook.cgi?Value=II.3,25&VType=IE&Formula=&AllowExtra=on&Units=SI[retrieved on Feb. 14, 2017].

* cited by examiner

DEVICE AND METHOD FOR GENERATING A PLASMA JET

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A READ-ONLY OPTICAL DISC OR AS A TEXT FILE VIA THE OFFICE ELECTRONIC FILING SYSTEM

Not Applicable

STATEMENT REGARDING PRIOR DISCLOSURES BY THE INVENTOR OR A JOINT INVENTOR

Not Applicable

BACKGROUND OF THE INVENTION

Field of the Invention

The invention relates to a device and a method for generating a plasma jet, particularly a non-thermal atmospheric pressure plasma jet, an endoscope comprising a device for generating a plasma jet according to the invention, a method for manipulating a cavity, and a use of the device for generating a plasma jet in a cavity in order to manipulate the cavity.

Description of Related Art Including Information Disclosed Under 37 CFR 1.97 and 1.98

Non-thermal plasma jets are generated by igniting a plasma in a process gas flow, wherein a spatially confined (in a radial direction) plasma stream is emitted from the plasma generation device. In particular, this spatial confinement is the result of the surrounding air, wherein particularly electronegative oxygen molecules repel the negatively charged electrons.

Plasma jets according to the prior art are particularly used to manipulate surfaces, for example to sterilize or disinfect objects such as surgical instruments, implants, or parts of a human or animal body. In many applications, particularly medical applications, manipulation of surfaces within cavities, which are often difficult to access, is desired.

Document DE 10 2009 028462 A1 discloses a device for generating a cold plasma stream mixed with micro or nano particles comprising a central pin electrode or a pair of electrodes arranged at the outside of the device. Document WO 2011/015538 describes a device for generating a plasma jet comprising a pin electrode positioned centrally in a feed gas conduit and a rigid metal housing. Due to their mechanical rigidity, these devices are not suitable for use in cavities.

Documents US 2011/0018444 A1, WO 2011/092186, and U.S. Pat. No. 8,475,451 B2, relate to devices for generating plasma jets in flexible tubes, and documents US 2014/005481 A1 and EP 1293169 B1 relate to flexible endoscopes comprising devices for generation of plasma jets.

Therefore, the problem to be solved by the present invention is to provide an improved device and an improved method for generating a plasma jet allowing a specific plasma treatment of objects, particularly in a cavity, in a simple, cost-efficient manner, which overcome the above-stated disadvantages of the prior art.

BRIEF SUMMARY OF THE INVENTION

This problem is solved by the device and the endoscope of independent claims 1 and 9 as well as by the methods of claims 11 and 14, and the use of claim 15. Further aspects and embodiments of the invention are addressed by the dependent claims 2 to 8, 18, and 12 to 13. The aspects and embodiments are described hereafter.

A first aspect of the invention relates to a device for generating a plasma jet, wherein the device for generating a plasma jet comprises a first conduit, which comprises a first outlet, and a second conduit, which comprises at least one second outlet, wherein the first conduit is arranged inside the second conduit, such that a first flow channel is provided inside the first conduit, and a second flow channel is provided in the space between the first conduit and the second conduit, and wherein the device comprises a first electrode, particularly a high voltage driven electrode, and a second electrode, particularly a grounded electrode, for generating an electric field in a feed gas flow provided in the first flow channel in order to generate a plasma jet from the feed gas flow, wherein the device is adapted to provide a curtain gas flow at the at least one second outlet surrounding the plasma jet emerging from the first outlet. Therein, the first electrode is positioned radially outside of the first flow channel, and the radial distance of the second electrode from a longitudinal axis of the first conduit is larger than the radial distance of the first electrode from the longitudinal axis.

Therein the term 'radial distance' refers to a minimal radial distance for arrangements, in which the first and/or second electrode is irregularly shaped and/or displaced from the longitudinal axis. In other words: the second electrode is positioned radially outside of the first electrode.

That is, the first conduit comprises a longitudinal axis, and the first electrode is positioned outside of the first flow channel in a radial direction with respect to the longitudinal axis of the first conduit.

The term 'curtain gas flow' describes a gas flow which is adapted to surround the plasma jet emerging from the first outlet. Therein, the curtain gas flow may comprise or consist of any gas or gas mixture, regardless of its ability to be ionized and/or form a plasma.

Depending on the applied voltage, the geometry of the device and the properties of the curtain gas, the curtain gas may or may not form a plasma when the electric field is generated by the first and second electrode of the device.

In particular, the device for generating a plasma jet is adapted to generate a non-thermal plasma jet. Therein, the term 'non-thermal' describes a plasma jet having a gas temperature that is orders of magnitude lower than the electron temperature. In particular, the gas temperature generated by the plasma jet is in the range of 10° C. to 45° C.

The device for generating a plasma jet is adapted to generate a low or atmospheric pressure plasma jet. That is, the pressure of the atoms and/or molecules comprised in the plasma is in a range of 100 mbar to 1200 mbar.

Therein, the plasma jet may comprise ions, free electrons, and/or metastable species generated by electronic transitions induced by the applied voltage.

In certain embodiments, the first conduit and the second conduit comprise a circular cross-section. Alternatively, the first and/or the second conduit may comprise a non-circular cross-section, particularly a polygonal or oval cross-section.

In particular, the free inner bore of the second conduit is larger than the outer diameter of the first conduit and/or the first electrode.

The first electrode of the device is positioned radially outside of the first flow channel. That is, the first electrode may be positioned on the inside wall of the first conduit towards the first flow channel, or the first electrode may be positioned on the outside wall of the first conduit towards the second flow channel, or the first electrode may be embedded in the first conduit, or the first electrode may be positioned in the second flow channel. The first electrode may also be partially embedded in the wall of the first conduit.

Therefore, the first flow channel contains free space, which is particularly not obstructed by a pin electrode. This is especially advantageous if the device is used as an endoscope or as part of an endoscope, since the free space can be used to position for example a sensing and/or manipulation device.

The electric field between the first electrode and the second electrode can be generated by applying a voltage between the first electrode and the second electrode, particularly by applying a voltage to the first electrode, wherein the second electrode serves as a grounded electrode.

In particular, the electric field is located in at least a part of the first flow channel, that is within at least a part of the first conduit, or the electric field is located at the first outlet of the first conduit. Thereby, a plasma is generated by at least a part of the atoms and/or molecules of the feed gas by means of the electric field. In particular, at least a part of the atoms and/or molecules of the feed gas are ionized by means of the electric field.

Surprisingly, it was found that the electric field in the first conduit or at the first outlet of the first conduit of the device according to the present invention is sufficient to ignite a plasma in the feed gas flow.

The device is adapted to provide a curtain gas flow in the second flow channel, wherein the curtain gas flow emerges from the at least one second outlet. By means of the arrangement of the second flow channel in the space between the first conduit and the second conduit, the curtain gas flow emerging from the at least one second outlet restricts the radial diffusion of the plasma jet emerging from the first outlet, which particularly results in a radially confined plasma jet in a cavity. Therein, the curtain gas may or may not form a plasma.

In certain embodiments, the wall of the first electrode is continuous in a circumferential direction. Thus, for example, the first electrode may be ring-shaped. Alternatively, the first electrode may contain openings in its wall and/or may consist of at least two sections in the circumferential direction.

In certain embodiments, the first electrode is positioned between the first flow channel and the second flow channel in a radial direction with respect to the longitudinal axis of the first flow channel.

In certain embodiments, the second electrode is positioned on the inside and/or on the outside of the second conduit. That is, the second electrode may be positioned on the inside wall of the second conduit towards the second flow channel, or the second electrode may be positioned on the outside wall of the second conduit, or the second electrode may be embedded in the wall of the second conduit. The second electrode may also be partially embedded in the wall of the second conduit.

In certain embodiments, the second conduit is partially or completely surrounded by the second electrode.

In certain embodiments, the wall of the second electrode is continuous in a circumferential direction. Thus, for example, the second electrode may be ring-shaped. Alternatively, the second electrode may contain openings in its wall and/or may consist of at least two sections in the circumferential direction.

In certain embodiments, the second electrode is a coil of wire, which is wound around the second conduit.

In certain embodiments, the second electrode is an electrically conductive outer protection sheath of the second conduit. In certain embodiments, the housing of the device for generating a plasma jet, particularly the housing of the second conduit, serves as a second electrode.

In certain embodiments, the at least one second outlet is arranged coaxially around the first outlet. That is the first outlet and the at least one second outlet extend around a common center point. Alternatively, in a non-coaxial arrangement, the first outlet may be arranged around a center point which does not coincide with the center point of the at least one second outlet.

In certain embodiments, the first outlet is surrounded by the at least one second outlet.

In certain embodiments, at least a part of the second conduit comprises a flexible section, wherein the bending stiffness of the flexible section is such that the flexible section can be bent by a bending radius in the range of 10 mm to 100 mm. Therein the term 'bending radius' refers to the bending radius with respect to the longitudinal axis of the second conduit. The term 'bending stiffness' refers to the resistance of the flexible section against bending deformation.

In particular: also the first conduit comprises a respective flexible section radially overlapping with the flexible section of the second conduit, wherein the bending stiffness of the flexible section of the first conduit is such that the respective flexible section can be bent by a respective bending radius, more particularly in the range of 10 mm to 100 mm.

A flexible section of the second conduit and/or the first conduit allows the device to be flexibly bent, particularly in a cavity. This is especially advantageous if the device is incorporated in an endoscope or used as an endoscope.

The first conduit and/or the second conduit may further comprise at least one rigid section characterized by a bending radius of more than 100 mm.

In certain embodiments, the maximum radial extension, particularly the maximum outer diameter, of the second conduit, is 10 mm or less, particularly 4 mm or less. If the second electrode is positioned radially outside of the second conduit, i.e. on the outside wall of the second conduit, the maximum radial extension is defined by the extension of the second conduit and the second electrode.

Such outer dimensions of the second conduit allow the device to be inserted into small-sized cavities. This is especially advantageous if the device is incorporated in an endoscope or used as an endoscope.

In certain embodiments, the first electrode is arranged at a distance, particularly an axial distance, from the first outlet, wherein the distance equals at least the maximum radial extension of the first conduit.

Advantageously, the distance between the first electrode and the first outlet prevents electric flashover between the first electrode and the first outlet. Thereby, in particular, flashover between the first electrode and a surface of a cavity, in which the device is inserted, is prevented. For example, when the device is used as an endoscope or as a part of an endoscope in medical applications, this is advantageous to prevent flashover to surfaces of a patient body, and therefore prevents damage to the patient.

In certain embodiments, an electrically insulating material is positioned between the first electrode and the first outlet.

In certain embodiments, the first electrode is arranged at a distance from the first outlet, wherein the distance equals at least the maximum radial extension of the first conduit, and an electrically insulating material is positioned between the first electrode and the first outlet.

In certain embodiments, the electrically insulating material is a part of the first conduit.

In certain embodiments, the insulating material is comprised in an insulating part.

In certain embodiments, the insulating part comprises wings and/or holes forming at least two second outlets. These wings or holes allow passage of the curtain gas through the respective section of the second flow channel, in which the insulating part is arranged.

In certain embodiments, the insulating part is custom-fit to the first conduit, particularly the first capillary, and/or to the second conduit, particularly the second capillary.

In certain embodiments, the first electrode comprises, particularly is coated with, an electrically insulating material. This advantageously prevents direct flashover through the gas-filled space between the first conduit and the second conduit, that is through the second flow channel.

In certain embodiments, the insulating part is designed such that a gas permeable opening is positioned between the insulating part and the inner wall of the second conduit, particularly the second capillary.

Advantageously, the insulating material prevents electric flashover between the first electrode and the first outlet. Thereby, in particular, flashover between the first electrode and a surface of a cavity, in which the device is inserted, is prevented. For example, when the device is used as an endoscope or as a part of an endoscope in medical applications, this is advantageous to prevent flashover to surfaces of a patient body, and therefore prevents damage to the patient.

In certain embodiments, the first conduit comprises a first capillary and a first tubing, wherein the first tubing is adapted to be connected to a feed gas reservoir, such that a feed gas flow can be provided in the first tubing, and wherein the first tubing is connected to the first capillary at a first junction, such that the feed gas flow can be provided in the first capillary, and wherein the first electrode is positioned at the first capillary or attached to the first capillary. Therein the first tubing and the first capillary constitute the first flow channel. In particular the flexible section of the first conduit is the first tubing. In particular, the flexible section of the second conduit is the second tubing.

In particular, the free inner bore of the second capillary is larger than the outer diameter of the first capillary and/or the first electrode.

In certain embodiments, the device for generating a plasma jet comprises a front module, particularly a rigid front module, which comprises the first capillary, the second capillary, the first electrode, and the second electrode. In certain embodiments, the front module has a length in the range between 2 mm and 10 mm. In certain embodiments, the front module comprises the first and the second capillary, wherein the first and the second capillary are concentrically joined. In certain embodiments, the front module comprises two concentrically arranged flexible tubes.

In certain embodiments, the first electrode is positioned at an axial distance of at least the maximal extension of the first conduit from the first junction.

Advantageously, the axial distance prevents plasma formation in the first conduit, which could result in unfavorable interactions between the plasma and the material of the first conduit, particularly the first tubing.

In certain embodiments, the second conduit comprises a second capillary and a second tubing, wherein the second tubing is adapted to be connected to a curtain gas reservoir, such that a curtain gas flow can be provided in the second tubing, and wherein the second tubing is connected to the second capillary at a second junction, such that the curtain gas flow can be provided in the second capillary. Therein the second tubing and the second capillary constitute the second flow channel.

In particular, the inner diameter of the second tubing is larger than the outer diameter of the first tubing, such that a gas-permeable second flow channel is formed between the first tubing and the second tubing.

In certain embodiments, the device for generating a plasma jet further comprises an electrical conductor for electrically connecting the first electrode to a voltage source, wherein the electrical conductor is wound helically around at least a part of the first conduit in a plurality of windings, particularly wherein neighboring windings are arranged at an axial distance of 1 mm or less. In particular, the electrical conductor is a wire.

An arrangement of the electrical conductor in windings around the first conduit advantageously allows a flexible segment of the first conduit, for example a tubing or a section of a tubing, to be bent without restriction of flexibility by the electrical conductor.

A dense arrangement of neighboring windings of the electrical conductor at a small distance or a shielding material advantageously minimizes the electrical field generated by the electrical conductor in the respective section of the first conduit, which prevents formation of a plasma in the respective section of the first conduit. Plasma formation is desired only at the first electrode. A plasma generated at other locations within the first conduit may result in degradation of material of the first conduit, particularly the tubing, which would increase maintenance costs of the device.

In certain embodiments, the device for generating a plasma jet further comprises an electrical conductor for electrically connecting the first electrode to a voltage source, wherein the electrical conductor is positioned in parallel to the first conduit, wherein the electrical conductor comprises a shielding material, which is adapted to shield an electric field provided by the electrical conductor.

In certain embodiments, the device for generating a plasma jet further comprises an electrical conductor for electrically connecting the first electrode to a voltage source, wherein the electrical conductor is comprised in a coating of the first conduit or a mesh surrounding the first conduit.

In certain embodiments, the electrical conductor is embedded in the material of the first conduit.

A second aspect of the invention relates to an endoscope, comprising a device for generating a plasma jet according to the first aspect of the invention, such that a plasma jet can be generated in a cavity by means of the device for generating a plasma jet, when the endoscope is at least partially inserted in the cavity. In particular, the device for generating a plasma jet is positioned in an insertion tube of the endoscope Therein, the term 'insertion tube' refers to a segment of the endoscope, which is adapted to be inserted into a cavity.

In certain embodiments, the endoscope is a flexible endoscope.

In certain embodiments, the endoscope comprises a sensing and/or manipulation device, particularly a micromechanical tool, an optical device, or a liquid channel adapted to provide a liquid at a proximal end of the endoscope, wherein the sensing and/or manipulation device is positioned or positionable in the first conduit of the device for generating a plasma jet. In particular, the first conduit serves an instrument channel of the endoscope.

In certain embodiments, the endoscope comprises a liquid channel, which is positioned in the first conduit. Therein the term 'liquid channel' designates a channel which is adapted to transport a liquid. Such a liquid channel can be used to provide a liquid at the proximal end of the endoscope. In particular, the liquid can be used for flushing the cavity, in which the endoscope is inserted.

In certain embodiments, the sensing and/or manipulation device is retractable in the first conduit. Due to the arrangement of the first electrode, the first conduit of the device for generating a plasma jet according to the present invention, which does not comprise a central pin electrode, contains space, in which the sensing and/or manipulation device of the endoscope may be inserted.

In certain embodiments, the sensing and/or manipulation device is positionable at the first and the at least one second outlet, that is at the proximal side of the endoscope.

A third aspect of the invention relates to a method for generating a plasma jet by means of a device for generating a plasma jet according to the first aspect of the invention, wherein a feed gas flow of a feed gas is provided in the first flow channel, an electric field is generated in the feed gas flow by applying a voltage between the first electrode and the second electrode, such that a plasma jet is generated from the feed gas flow by means of the electric field, and a curtain gas flow of a curtain gas surrounding the plasma jet emerging from the first outlet is provided at the at least one second outlet.

In certain embodiments, the feed gas is characterized by an ignition voltage that is lower than the ignition voltage of the curtain gas. In the context of the present specification, the term 'ignition voltage' describes the voltage at which plasma is generated, that is ignited, in the respective gas. Plasma formation of the feed gas at the first electrode is desired, wherein plasma formation of the curtain gas is not desired. However, in some embodiments, a plasma may also be formed in the curtain gas.

In particular, the ignition voltage of the feed gas and the curtain gas depends on the ionization energies of components of the feed and curtain gas as well as on their tendency to form metastable species by electronic transitions.

In certain embodiments, the curtain gas comprises molecules, which bind electrons especially well.

In certain embodiments, the curtain gas comprises $O_2$, $Cl_2$, or $F_2$, particularly $O_2$. In particular, these molecules comprise atoms characterized by a high electronegativity, which results in a higher than average tendency of these molecules to bind electrons.

In certain embodiments, the curtain gas comprises $O_2$, $Cl_2$, or $F_2$ or $CO_2$, particularly $O_2$ or $CO_2$, more particularly $CO_2$. In particular, these molecules comprise atoms characterized by a high electronegativity, which results in a higher than average tendency of these molecules to bind electrons.

In certain embodiments, the curtain gas comprises $CO_2$.

In certain embodiments, the curtain gas comprises $O_2$.

In certain embodiments, the curtain gas comprises gas atoms, which comprise an electronegativity of 3 or more on an Allred-Rochow scale.

In certain embodiments, the curtain gas comprises gas atoms or molecules, which comprise an affinity to bind electrons. Electron affinity of an atom or molecule means that energy is necessary to remove an electron from the negatively charged atom or molecule.

In certain embodiments, the curtain gas is composed of a single species of atoms of molecules.

In certain embodiments, the curtain gas is a gas mixture comprising more than one species of atoms or molecules.

In certain embodiments, the curtain gas is a molecular gas or a gas mixture comprising a molecular gas, particularly air or $CO_2$.

The use of a curtain gas comprising atoms or molecules with a tendency to bind electrons advantageously facilitates a spatial restriction of the plasma jet.

In certain embodiments, the feed gas is a noble gas, particularly helium, argon or neon.

In certain embodiments, the gas flow rate of the feed gas and/or the curtain gas is less than 3 standard liter/min, particularly 0.05 standard liter/min to 1 standard liter/min, more particularly 0.1 standard liter/min to 1 standard liter min.

In certain embodiments, the gas flow rate of the curtain gas is identical to the gas flow rate of the feed gas.

In certain embodiments, the gas flow rate of the curtain gas is different from the gas flow rate of the feed gas.

In certain embodiments, an AC voltage is applied to the first electrode, particularly at a frequency in the range of 100 Hz to 10 MHz, particularly above 16 kHz.

Advantageously, a frequency above 16 kHz is above the human auditory threshold, which reduces unpleasant noise, particularly when the method is used for patient diagnosis or treatment, i.e. in a medical endoscopic procedure.

In certain embodiments, a voltage signal is applied to the first electrode, particularly a sine voltage signal, a pulsed voltage signal, or a square voltage signal.

A fourth aspect of the invention relates to a method for manipulating a cavity, particularly sterilizing or disinfecting a cavity, more particularly a cavity of a human or animal body, wherein a plasma jet is generated inside of the cavity by means of a method for generating a plasma jet according to the third aspect of the invention, and wherein an inner surface of the cavity is contacted by the plasma jet, such that the inner surface is manipulated, particularly sterilized or disinfected, by means of the plasma jet.

A fifth aspect of the invention relates to a use of the device for generating a plasma jet according to the first aspect of the invention in a cavity in order to manipulate, particularly sterilize or disinfect, the cavity.

A sixth aspect of the invention relates to a method for manipulating a cavity, particularly sterilizing or disinfecting a cavity, outside of the human and/or animal body, wherein a plasma jet is generated inside of the cavity by means of a method for generating a plasma jet according to the third aspect of the invention, and wherein an inner surface of the cavity is contacted by the plasma jet, such that the inner surface is manipulated, particularly sterilized or disinfected, by means of the plasma jet.

A seventh aspect of the invention relates to a use of the device for generating a plasma jet according to the first aspect of the invention in a cavity outside of the human and/or animal body in order to manipulate, particularly sterilize or disinfect, the cavity.

BRIEF DESCRIPTION OF THE SEVERAL VIEWS OF THE DRAWING(S)

The invention is further illustrated by the following figures, from which further embodiments and advantages can be drawn. These examples are meant to illustrate the invention but not to limit its scope.

Figure 2:
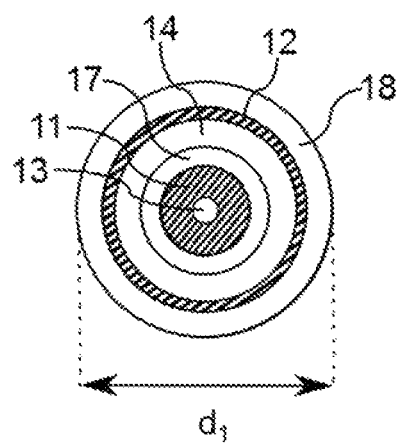
Figure 3:
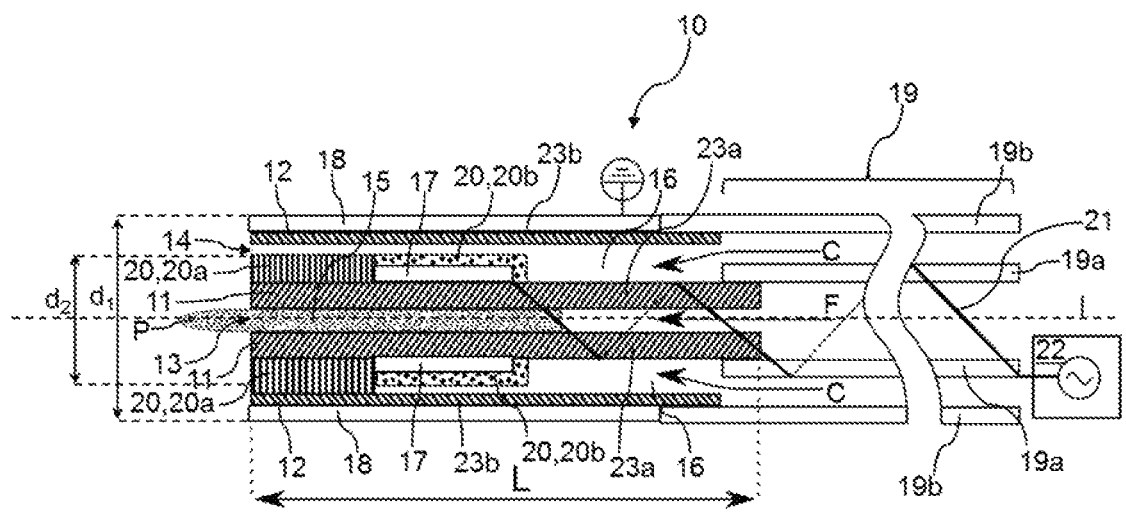
Figure 4:
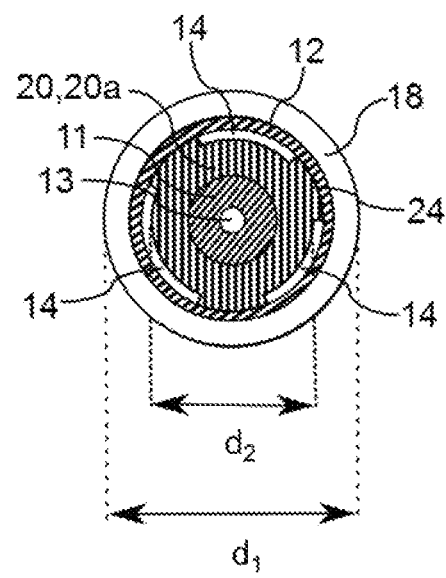

FIG. 1 shows an axial cross-section of a device for generating a plasma jet in a first embodiment, FIG. 2 shows a radial cross-section of the device for generating a plasma jet in the first embodiment, FIG. 3 shows an axial cross-section of a device for generating a plasma jet in a second embodiment comprising an insulating part, FIG. 4 shows a radial cross-section of the device for generating a plasma jet in the second embodiment.

DETAILED DESCRIPTION OF THE INVENTION

FIG. 1 shows an axial cross-section of a device 10 for generating a plasma jet P according to the present invention. The device 10 comprises a first conduit 11 shaped as a hollow cylinder, which is arranged around a longitudinal axis I, and a second conduit 12 shaped as a hollow cylinder, wherein the second conduit 12 is concentrically arranged around the first conduit 11. The first conduit 11 consists of a first capillary 23a having a length L, and a first tubing 19a, wherein the first capillary 23a is connected to the first tubing 19a. The first tubing 19a is adapted to be connected to a feed gas reservoir, such that a feed gas flow F can be provided in the first flow channel 15 formed by the first conduit 11. The first conduit 11 comprises a first outlet 13 at the distal end of the first capillary 23a with respect to the connection to the first tubing 19a.

The device 10 further comprises a first electrode 17, which is positioned on the outer wall of the first capillary 23a at an axial distance from the first outlet 13, which prevents flashover from the first electrode 17 to a surface, to which the plasma jet P is applied by means of the device 10. In an alternative embodiment, the first electrode 17 comprises the same length as the first capillary 23a. The first electrode 17 is electrically connected to a voltage source 22 by means of an electrical conductor 21 in form of a wire, which is helically wound around the first conduit 11 in a plurality of windings. This arrangement provides flexibility of the flexible section 19 of the device, and minimizes the electrical field provided by the electrical conductor 21 in the first conduit 11.

The second conduit 12 consists of a second capillary 23b, which is connected to the second tubing 19b. The second tubing 19b forms a flexible section 19 of the second conduit 12. The second tubing 19b is adapted to be connected to a curtain gas reservoir, such that a curtain gas flow C can be provided in a second flow channel 16 in the second conduit 12. Therein, the second flow channel 16 is arranged concentrically around the first flow channel 15.

The device 10 further comprises a second electrode 18 arranged on the outer wall of the second capillary 23b, wherein the second electrode 18 is grounded. The second electrode 18 is characterized by a first diameter $d_1$ in the radial direction.

By applying a voltage to the first electrode 17, an electrical field is generated between the first electrode 17 and the second electrode 18. As a result of a boundary effect, the electric field extends into a part of the first conduit 11 near the proximal edge of the first electrode 17 with respect to the first outlet 13. This leads to the generation of a plasma jet P in the first flow channel 15 if a feed gas flow F is provided in the first flow channel 15. A curtain gas flow C provided in the second flow channel 16 emerges from the second outlet 14 and surrounds the plasma jet P emerging from the first outlet 13. In particular if an electronegative curtain gas is used to provide the curtain gas flow C, the plasma jet P is spatially confined in the radial direction as a result of the curtain gas flow C.

FIG. 2 shows a radial cross-section of the device 10 shown in FIG. 1 viewed from the side of the first outlet 13 and the second outlet 14. The concentric arrangement of the first outlet 13, the wall of the first conduit 11, the first electrode 17, the second outlet 14, the wall of the second conduit 12, and the second electrode 18, from the center to the periphery, is shown.

FIG. 3 shows an axial cross-section of a device 10 for generating a plasma jet P of the present invention in a further embodiment. The device 10 is designed analogously to the device 10 shown in FIGS. 1 and 2, except that the device further comprises an insulating part 20 comprising an electrically insulating material. The insulating part 20 comprises a first insulating part 20a positioned between the first electrode 17 and the first outlet 13 in the axial direction, and between the outer wall of the first conduit 11 and the inner wall of the second conduit 12 in the radial direction. The insulating part further comprises a second insulating part 20b in form of a coating of the first electrode 17. The insulating part 20 prevents flashover from the first electrode 17 to a surface, to which the plasma jet P is applied by means of the device 10.

FIG. 4 shows a radial cross-section of the device 10 depicted in FIG. 3 viewed from the side of the first outlet 13 and second outlet 14. The first outlet 13, the wall of the first conduit 11, and the first insulating part 20a are arranged concentrically. The first insulating part 20a comprises three second outlets 14, which are arranged around the circumference of a circle having a second diameter $d_2$. The second outlets 14 are separated by three wings 24, which connect the first insulating part 20a to the wall of the second conduit 12. The second diameter corresponds to the diameter of the first insulating part 20a without wings 24. The second electrode 18 is arranged concentrically around the outer wall of the second conduit 12.

The second outlets 14 are arranged such that the curtain gas flow C provided in the second flow channel 16 emerges from the second outlets 14 and at least partially surrounds the plasma jet P emerging from the first outlet 13, such that the plasma jet P is spatially confined in the radial direction.

LIST OF REFERENCE SIGNS

| | |
|---|---|
| 10 | Device for generating a plasma jet |
| 11 | First conduit |
| 12 | Second conduit |
| 13 | First outlet |
| 14 | Second outlet |
| 15 | First flow channel |
| 16 | Second flow channel |
| 17 | First electrode |
| 18 | Second electrode |
| 19 | Flexible section |
| 19a | First tubing |
| 19b | Second tubing |
| 20 | Insulating part |
| 20a | First insulating part |
| 20b | Second insulating part |

| | |
|---|---|
| 21 | Electrical conductor |
| 22 | Voltage source |
| 23a | First capillary |
| 23b | Second capillary |
| 24 | Wing |
| P | Plasma jet |
| F | Feed gas flow |
| C | Curtain gas flow |
| L | Longitudinal axis |
| L | Length |
| $d_1$ | First diameter |
| $d_2$ | Second diameter |

The invention claimed is:

1. A device for generating a plasma jet, comprising a first conduit, which comprises a first outlet, and a second conduit, which comprises at least one second outlet, wherein the first conduit is arranged inside the second conduit, such that a first flow channel is provided inside the first conduit, and a second flow channel is provided in the space between the first conduit and the second conduit, and wherein the device comprises a first electrode and a second electrode for generating an electric field in a feed gas flow provided in the first flow channel in order to generate a plasma jet from the feed gas flow, wherein the device is adapted to provide a curtain gas flow at the second outlet surrounding the plasma jet emerging from the first outlet, wherein the first electrode is positioned radially outside of the first flow channel,
characterized in that
the radial distance of the second electrode from a longitudinal axis of the first conduit is larger than the radial distance of the first electrode from said longitudinal axis,
and that the maximum radial extension of the second conduit is 10 mm or less, particularly 4 mm or less.

2. The device for generating a plasma jet according to claim 1, characterized in that the first electrode is positioned between the first flow channel and the second flow channel.

3. The device for generating a plasma jet according to claim 1, characterized in that the second outlet is arranged coaxially around the first outlet.

4. The device for generating a plasma jet according to claim 1, characterized in that at least a part of the second conduit comprises a flexible section, wherein the bending stiffness of the flexible section is such that the flexible section can be bent by a bending radius in the range of 10 mm to 100 mm.

5. The device for generating a plasma jet according to claim 1, characterized in that
a. the first electrode is arranged at a distance from the first outlet, wherein the distance equals at least the maximum radial extension of the first conduit, and/or
b. an electrically insulating material is positioned between the first electrode and the first outlet.

6. The device for generating a plasma jet according to claim 1, characterized in that the device for generating a plasma jet further comprises an electrical conductor for electrically connecting the first electrode to a voltage source, wherein the electrical conductor
a. is wound helically around the first conduit in a plurality of windings, and/or
b. is comprised in a coating of the first conduit or a mesh surrounding the first conduit.

7. The device for generating a plasma jet according to claim 1, characterized in that the device for generating a plasma jet further comprises an electrical conductor for electrically connecting the first electrode to a voltage source, wherein the electrical conductor
a. is positioned in parallel to the first conduit, wherein the electrical conductor comprises a shielding material, which is adapted to shield an electric field provided by the electrical conductor, and/or
b. is comprised in a coating of the first conduit or a mesh surrounding the first conduit.

8. An endoscope, comprising a device for generating a plasma jet according to claim 1, such that a plasma jet can be generated in a cavity by means of the device for generating a plasma jet, when the endoscope is at least partially inserted in the cavity.

9. The endoscope according to claim 8, wherein the endoscope comprises a sensing and/or manipulation device, particularly a micromechanical tool, an optical device, or a liquid channel adapted to provide a liquid at a proximal end of the endoscope, wherein the sensing and/or manipulation device is positioned or positionable in the first conduit of the device for generating a plasma jet.

10. A method for generating a plasma jet by means of a device for generating a plasma jet according to claim 1, wherein
a feed gas flow of a feed gas is provided in the first flow channel,
an electric field is generated in the feed gas flow by applying a voltage between the first electrode and the second electrode, such that a plasma jet is generated from the feed gas flow by means of the electric field,
a curtain gas flow of a curtain gas surrounding the plasma jet emerging from the first outlet is provided at the second outlet.

11. The method for generating a plasma jet according to claim 10, wherein the curtain gas comprises $O_2$, $Cl_2$, $F_2$ or $CO_2$, particularly $O_2$ or $CO_2$, more particularly $CO_2$.

12. The method for generating a plasma jet according to claim 10, wherein the gas flow rate of the feed gas and/or the curtain gas is less than 3 standard liter/min, particularly 0.05 standard liter/min to 1 standard liter/min, more particularly 0.1 standard liter/min to 1 standard liter/min.

13. The method for manipulating a cavity, particularly sterilizing or disinfecting a cavity, wherein a plasma jet is generated inside of the cavity by means of a method for generating a plasma jet according to claim 10, and wherein an inner surface of the cavity is contacted by the plasma jet, such that the inner surface is manipulated, particularly sterilized or disinfected, by means of the plasma jet.

14. Use of the device for generating a plasma jet according to claim 1 in a cavity in order to manipulate, particularly sterilize or disinfect, the cavity.

* * * * *